(12) United States Patent
Maaskamp et al.

(10) Patent No.: US 9,216,105 B2
(45) Date of Patent: *Dec. 22, 2015

(54) RECTOCELE AND CYSTOCELE DEVICE

(71) Applicants: Ryan Maaskamp, San Francisco, CA (US); Armand Maaskamp, Napa, CA (US); Gervasio Salgado, Marbella (ES)

(72) Inventors: Ryan Maaskamp, San Francisco, CA (US); Armand Maaskamp, Napa, CA (US); Gervasio Salgado, Marbella (ES)

(73) Assignee: Medicele, LLC., Napa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/205,939

(22) Filed: Mar. 12, 2014

(65) Prior Publication Data

US 2014/0261445 A1    Sep. 18, 2014

Related U.S. Application Data

(63) Continuation-in-part of application No. 13/803,890, filed on Mar. 14, 2013, now Pat. No. 9,072,582.

(60) Provisional application No. 61/887,849, filed on Oct. 7, 2013, provisional application No. 61/786,253, filed on Mar. 13, 2013.

(51) Int. Cl.
 *A61F 2/00* (2006.01)
 *A61F 6/12* (2006.01)
 *A61F 6/08* (2006.01)

(52) U.S. Cl.
 CPC .... *A61F 6/12* (2013.01); *A61F 6/08* (2013.01)

(58) Field of Classification Search
 CPC ....... A61F 2/00; A61F 2/0004; A61F 2/0031; A61F 2/0036; A61F 2/005; A61F 2/0013; A61B 17/4241

USPC .............. 600/29–32, 37, 184, 201, 207, 210; 606/205–207

See application file for complete search history.

(56) References Cited

U.S. PATENT DOCUMENTS

| | | |
|---|---|---|
| 860,591 A | 7/1907 | Baird |
| 2,400,251 A | 5/1946 | Nagel |
| 2,494,393 A | 1/1950 | Lamson |
| 2,856,920 A | 10/1958 | Indelicato |
| 3,994,291 A | 11/1976 | Salmasian |
| 4,612,924 A | 9/1986 | Cimber |
| 4,669,478 A | 6/1987 | Robertson |

(Continued)

FOREIGN PATENT DOCUMENTS

| | | |
|---|---|---|
| EP | 0700669 A1 | 3/1996 |
| FR | 2228464 83 | 4/1976 |

*Primary Examiner* — John Lacyk
(74) *Attorney, Agent, or Firm* — Kenneth Altshuler

(57) ABSTRACT

A recto-cystocele device to address rectocele and cystocele disorder is described. The device generally comprise a handle and a paddle that are distinguished from one another by a bend in the recto-cystocele device which forms essentially an L-shaped unit, the bend possessing a sufficient radius to avoid contact with a pelvic region of the woman and the recto-cystocele device. The device further comprises an expandable sheath located on the paddle that after being inserted in a vagina of the woman and is expanded therein is in contact with at least an upper portion of the vagina that includes a posterior fornix of the vagina and a lower portion of the vagina that does not include the posterior fornix. The handle, which does not go into the vagina, is adapted to be manually manipulated by the woman to translate directional pressure against the posterior fornix and the lower portion of the vagina via the expandable sheath when expanded.

20 Claims, 20 Drawing Sheets

(56) References Cited

U.S. PATENT DOCUMENTS

| | | |
|---|---|---|
| 4,875,898 A | 10/1989 | Eakin |
| 4,920,986 A | 5/1990 | Biswas |
| 4,986,823 A | 1/1991 | Anderson |
| 5,364,146 A | 11/1994 | Brandorff |
| 5,603,685 A | 2/1997 | Tutrone, Jr. |
| 5,716,329 A | 2/1998 | Dieter |
| 5,988,169 A | 11/1999 | Anderson |
| 6,077,257 A | 6/2000 | Edwards |
| 6,168,586 B1 | 1/2001 | Hahnen |
| 6,676,594 B1 | 1/2004 | Zunker |
| 6,795,737 B2 | 9/2004 | Gielen |
| 7,179,219 B2 | 2/2007 | Matlock |
| 7,288,063 B2 | 10/2007 | Petros |
| 7,325,546 B2 | 2/2008 | Burbank |
| 7,513,868 B1 | 4/2009 | Fontenot |
| 7,634,049 B2 | 12/2009 | Galkin |
| 7,771,344 B2 | 8/2010 | Ziv |
| 7,981,024 B2 | 7/2011 | Levy |
| 8,302,608 B2 | 11/2012 | Harmanli |
| 8,360,954 B2 | 1/2013 | Kim |
| 2003/0078526 A1 | 4/2003 | Farley |
| 2005/0021080 A1 | 1/2005 | Feuer et al. |
| 2006/0025782 A1 | 2/2006 | Klein et al. |
| 2006/0211911 A1 | 9/2006 | Jao et al. |
| 2009/0216071 A1 | 8/2009 | Zipper |
| 2010/0174214 A1 | 7/2010 | Gabbay et al. |
| 2014/0275749 A1* | 9/2014 | Maaskamp et al. ............. 600/37 |

* cited by examiner

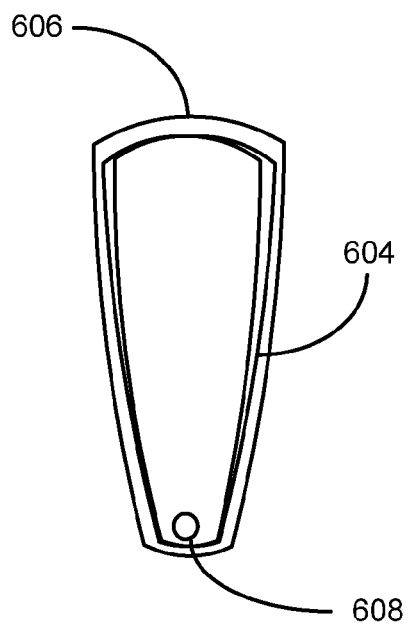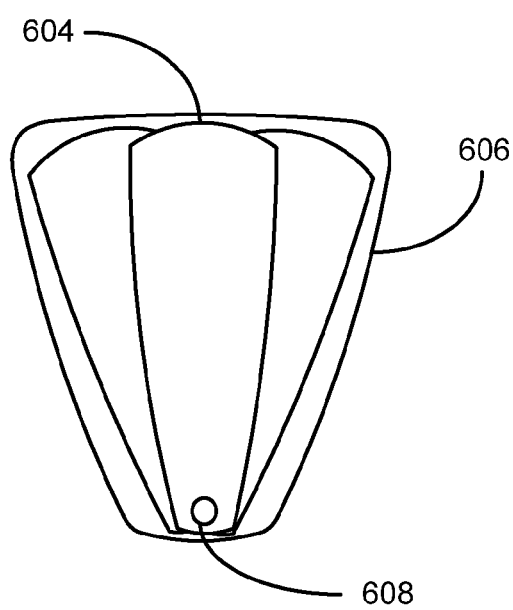
FIG. 6C  FIG. 6D

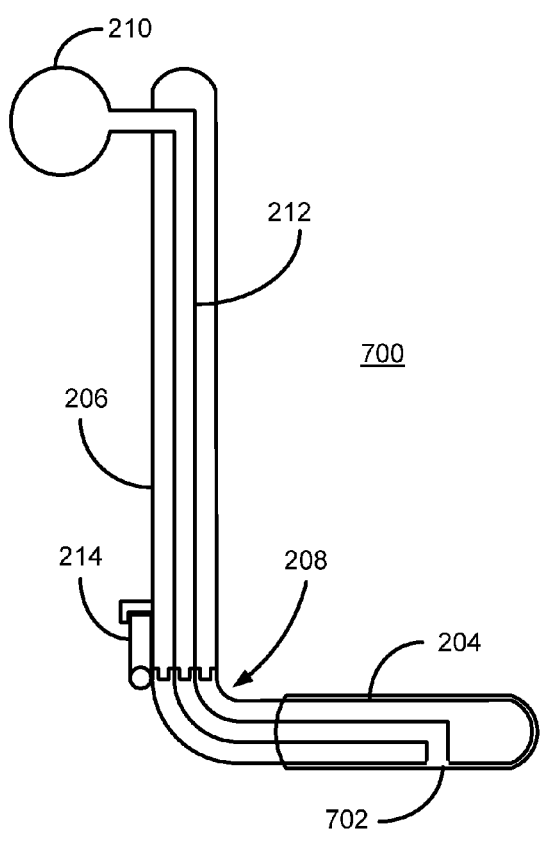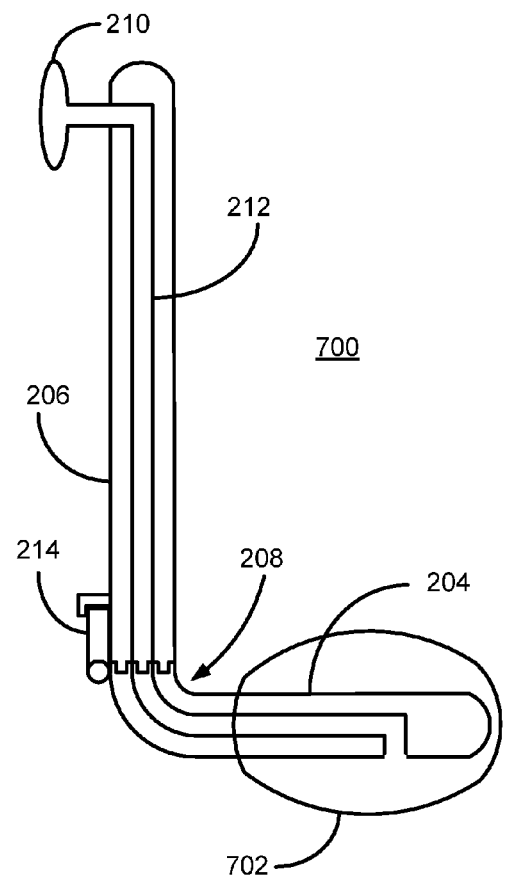
FIG. 7A  FIG. 7B

RECTOCELE AND CYSTOCELE DEVICE

CROSS-REFERENCE TO RELATED APPLICATIONS

This application claims priority to and the benefit of U.S. Non-provisional patent application Ser. No. 13/803,890, entitled: Rectocele Device, filed on Mar. 14, 2013 the entire disclosure of which is hereby incorporated by reference, U.S. Provisional Patent Application No. 61/786,253 entitled: Cystocele Device, filed on Mar. 13, 2013, the entire disclosure of which is hereby incorporated by reference, and U.S. Provisional Patent Application No. 61/887,849 entitled: Rectocele and Cystocele Device, filed on Oct. 7, 2013, the entire disclosure of which is hereby incorporated by reference.

FIELD OF THE INVENTION

The present invention is directed to a rectocele and cystocele device that is useful in reducing the effects of a rectocele which impair a woman's ability to move bowel and/or a cystocele which impair a woman's ability to urinate.

BACKGROUND OF THE INVENTION

Rectocele 104 in a roman 100 is a condition whereby the woman's rectum is prolapsed into the posterior wall of the woman's vagina. Rectocele is defined as bulging of the front wall of the rectum (rectovaginal wall) into the vagina. Rectocele is due to weakening of the pelvic support structures and thinning of the rectovaginal wall (the tissues separating the rectum from the vagina) and is primarily a result of childbirth, chronic constipation, and hysterectomy. The rectum ballooning into the vagina is often exacerbated during a bowel movement as shown in FIG. 1A. As a result, the woman may experience the sensation of pressure or protrusion within the vagina, and the occasional feeling that the rectum has not been completely emptied after a bowel movement. In more moderate cases, a woman may have difficulty passing stool because the attempt to evacuate pushes the stool into the rectocele instead of out through the anus.

In an attempt to aid with a bowel movement in cases of rectocele, a woman may insert her fingers into her vagina to manually press against the rectocele, which helps create a uniform pathway for stool to move out of the rectum. Because a rectocele may protrude to the right of left of the posterior wall of the vagina, by using the sense of touch in her fingers, a woman is able to reposition her fingers to the where the rectocele occurs. In other words, a woman is able to press against the rectocele with her fingers by taking advantage of bio-feedback in her fingers.

As shown in FIG. 1B, a cystocele 154 in a woman 100 is a condition whereby the woman's bladder prolapsed into the anterior wall of the women's vagina Cystocele 154 is defined as bulging of the back wall of the bladder (bladdervaginal wall) into the vagina. Cystocele is due to weakening of the pelvic support structures and thinning of the bladdervaginal wall (pubovesical fascia, the tissues separating the bladder from the vagina) and is primarily believed to be a result of childbirth. The bladder ballooning into the vagina causes discomfort and problems with emptying the bladder. The elastic tissues of the vagina may compensate for this tear for some time after the injury occurs. Because the hormone estrogen helps keep the elastic tissues around the vagina strong, a cystocele may not occur until menopause, when levels of estrogen decrease. There are no muscles around the vagina, except the bulbocavernosus muscles at the entrance to the vagina. The levator muscle passes around the vagina and the rectum and inserts into the levator plate, which can elevate rectum, the vagina and the bladder neck together. As a result, a bladder that has dropped from its normal position may cause two kinds of problems: unwanted urine leakage and incomplete emptying of the bladder. The pubocervical fascia provides back support to the mid urethra, allowing compression when abdominal pressure is increased. This prevents urine loss with sudden increases in pressure, as with coughs, sneezes, laughs, or moves in any way that puts pressure on the bladder. If this compression is lost by tissue tears, then stress incontinence results. If the base of the bladder herniates, then urine will sump down into the inside of the hernia, and bladder emptying will be impaired. The woman may experience the sensation of pressure or protrusion within the vagina, and the occasional feeling that the bladder has not been completely emptied after urination.

Though surgical procedures exist to repair rectoceles and cystoceles, in less severe cases, a number of optional devices currently exist to provide some rectocele and/or cystocele relief. One family of devices includes spoon-like devices, which are used just prior to a bowel movement to essentially when the bowel movement or urination is completed. Unlike the biofeedback of fingers to facilitate repositioning of pressure against the rectocele or the cystocele, spoon-like devices are unable to sense if a rectocele or cystocele is sliding to the right or left of the spoon. In one example, when a rectocele slides to the right or left of the spoon, the woman may press harder against her posterior rectovaginal wall with the spoon because she is not experiencing proper stool evacuation and cannot sense through bio-feedback that the rectocele has moved around the spoon, which then may cause damage to her posterior rectovaginal wall. The same problem applies to a cystocele.

Another family of devices used to address rectoceles includes pessaries, which are typically inflated balloons that provide static pressure on all surfaces of the vaginal canal (the rectovaginal wall, lateral walls and the bladdervaginal wall). Pessaries offer extended support to address rectoceles. Pessaries are not inserted into a vagina just prior to a bowel movement to the point of when a bowel movement is complete or prior to the point of urination or just when urination is complete. Rather, pessaries are left in the vagina for an extended period of time, sometimes being inserted in the morning and removed at night to being left in for days at a time, if not longer. Moreover, due to the static nature of pessaries, pessaries are unable to be manipulated to push prolapsing organs back into place once inserted in a vagina.

It is to innovations related to addressing passing a bowel movement in women suffering from a rectocele or urination in women suffering from a cystocele that the claimed invention is generally directed.

SUMMARY OF THE INVENTION

The present invention is directed to a rectocele/cystocele device that is useful in providing pressure against the rectocele to improve bowel movements in women or against the cystocele to improve urination events in women.

Embodiment of the present invention can therefore comprise a recto-cystocele device adapted to be inserted in a vagina of a woman through a vaginal opening, the recto-cystocele device comprising: a handle; a paddle, wherein the handle and the paddle are distinguished by a bend in the recto-cystocele device which forms essentially an L-shaped unit, the bend possessing a sufficient radius to avoid contact with a pelvic region of the woman and the recto-cystocele device; and an expandable sheath located on the paddle that after being inserted in a vagina of the woman and is expanded therein is in contact with at least a cervix and a portion of the vagina, the handle, which does not go into the vagina, is adapted to be manually manipulated by the woman to translate directional pressure against the cervix and the portion of the vagina via the expandable sheath when expanded.

Embodiments of the recto-cystocele device are contemplated to include: embodiments where the bend extends between 0.5 inches and 5.0 inches from the paddle, embodiments where the bend possesses a radius of between 0.5 inches and 3.0 inches, embodiments where the directional pressure is in a direction that lifts the pelvic floor away from the vaginal opening, embodiments where the directional pressure includes all directions in three dimensions but remains in contact with the cervix, embodiments further comprising a replaceable sleeve that covers the expandable sheath during each use, embodiments where the directional pressure is in a direction that supports a uterus, a rectrouterine pouch, a rectum all associated with the woman via the vagina, embodiments where the portion is at least 50% of the vaginal cavity, embodiments where the recto-cystocele device is adapted to be used essentially from just prior to a bowel movement of the woman to just after the bowel movement, embodiments where the recto-cystocele device is adapted to be used essentially from just prior to a urination event of the woman to just after the urination event, embodiments further comprising an inflation bulb disposed on the handle that is connected to the expandable sheath by way of a tube, embodiments further comprising an inflation bulb disposed on the handle that is connected to the expandable sheath by way of a tube wherein the inflation bulb is adapted to inflate the expandable sheath with air when the inflation bulb is manually squeezed, embodiments where, embodiments where the L-shaped unit possesses an angle that is essentially ninety degrees between the handle and the paddle, embodiments where the expandable sheath extends to at least the distal end of the paddle, embodiments where the expandable sheath is manually expanded and contracted, embodiments further comprising an inflation bulb connected to the handle via a flexible tube wherein a continuous pathway is formed between the inflation bulb and the expandable sheath.

Another embodiment of the present invention can therefore comprise a device to assist stool evacuation and urine voiding, the device comprising: a handle and a paddle, the handle and the paddle are delineated by a bend in the device; and an expandable sheath located on the paddle, the paddle adapted to be inserted through a vaginal opening in a vagina of a woman wherein the expandable sheath is expanded inside of the vagina to contact at least a cervix and a portion of the vagina, the handle adapted to be manipulated by the woman to lift the pelvic floor away from the vaginal opening via the expandable sheath when expanded, the handle not adapted to go in the vagina.

Embodiments of the device to assist stool evacuation and urine voiding are contemplated to include: embodiments where the handle adapted to not be in contact with a pelvic region of the woman, embodiments where the portion is at least 50% of the vagina, embodiments where the bend possesses a radius that extends sufficiently from the paddle to avoid contact with the pelvic region of the woman, embodiments where the handle and the paddle forms essentially an L-shaped unit, embodiments where the device is adapted to be used essentially from just before a bowel movement of the woman to just after the bowel movement or essentially from just before a urination event of the woman to just after the urination event which can further comprising a replaceable sleeve that covers the expandable sheath during each use and then can further comprising a means to retain the replaceable sleeve on the paddle.

Yet another embodiment of the present invention can therefore comprise a method to ease a defecation event or a urination event in a woman wherein the woman solely performs the method on herself, the method comprising: providing a rectocele/cystocele device possessing: a handle, a paddle wherein the handle and the paddle are delineated by a bend in the rectocele/cystocele device, and an expandable sheath disposed on the paddle; holding the handle; inserting the paddle and expandable sheath through a vaginal opening in a vagina of the woman prior to the defecation or the urination event when the woman experiences a desire to defecate or urinate wherein the handle remains outside of the vagina; expanding the sheath in the vagina; moving the expandable sheath in a first position to be in contact with a cervix of the woman and a portion of the vagina; manipulating the handle to adjust the cervix and the portion of the vagina in a second position via the expandable sheath wherein the handle avoids contact with a pelvic region of the woman; and withdrawing the paddle and expandable sheath from the vaginal opening following the defecation or the urination event.

Embodiments of the method to ease a defecation event or a urination event in a woman can further include: embodiments where the inserting step is performed within five minutes of the defecation or the urination event and the withdrawing step is performed within five minutes of the defecation or the urination event, embodiments further comprising covering the expandable sheath with an unused replaceable sleeve, embodiments further comprising manually expanding the sheath by squeezing a bulb located at the distal end of the handle.

Further embodiments contemplate a sheath possessing dual balloons or several sheaths wherein one balloon (or sheath) is in contact with a woman's posterior fornix (including cervix when present) and another balloon (or sheath) is in contact with a different part of the vaginal wall that does not include the posterior fornix.

BRIEF DESCRIPTION OF THE DRAWINGS

FIGS. 6A-6D illustratively depicts and embodiment of mechanical hardware adapted to expand an expandable sheath, consistent with embodiments of the present invention.

FIGS. 7A and 7B depict an alternative embodiment of a rectocele device, consistent with embodiments of the present invention.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving holding back rectoceles.

Figure 1A:
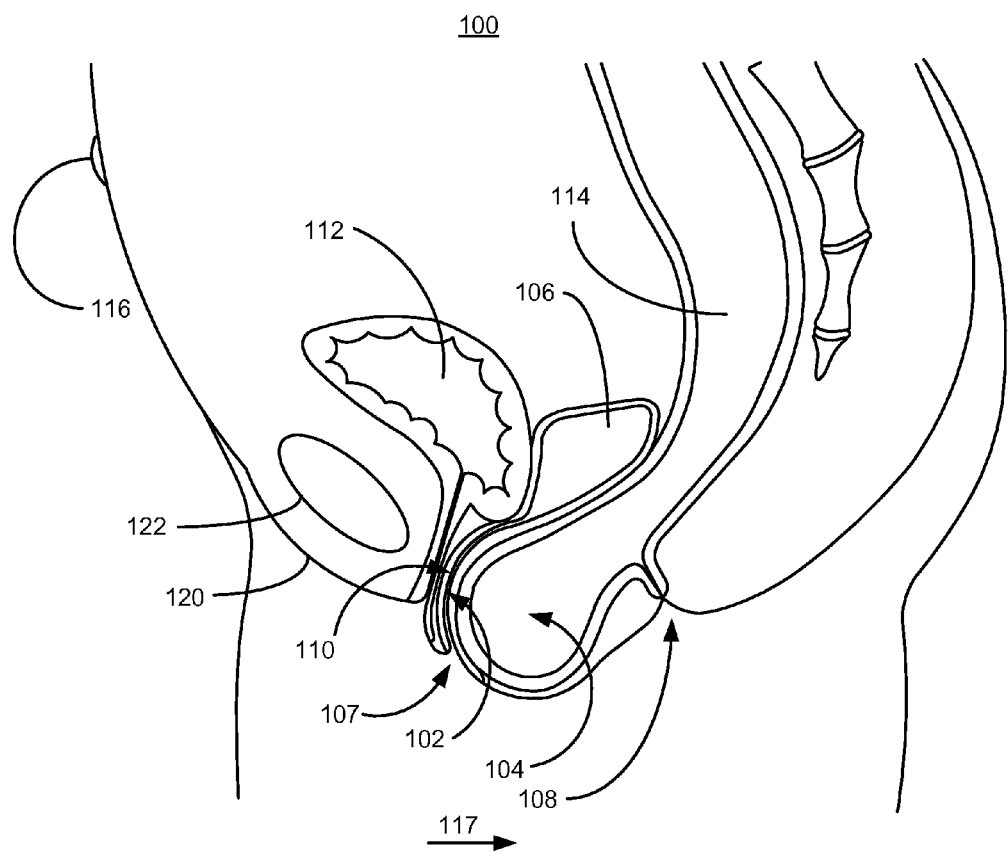
FIG. 1A depicts a cross section of a pelvic area of a woman suffering from a rectocele.

To illustrate an exemplary environment in which preferred embodiments of the present invention can be practiced, FIG. 1A depicts a cross section of a pelvic area of a woman 100 suffering from a rectocele 104. The rectocele 104 is shown bulging into the rectovaginal wall 102 of the vagina 106. The rectovaginal wall 102 is the septum between the vaginal vault (vagina) 106 and the rectal vault (rectum) 114 in the posterior direction 117 of the vagina 106. For reference, also shown herein are the bladder 112, the bladdervaginal wall 110, the vaginal opening 107, and the anus 108. Though not shown, the vagina 106 also has lateral walls of the vagina 106, which directionally extend towards the inner thighs of the woman 100. In other words, the rectovaginal wall 102 extends towards the posterior 117 and the bladdervaginal wall extends towards the anterior (pubic bone 122) of the woman 100, whereas, the lateral walls of the vagina 106 are orthogonal to the anterior/posterior direction. From the anterior side, also shown are the belly button 116, the pubic bone 122, and the mons veneris 120.

Figure 2:
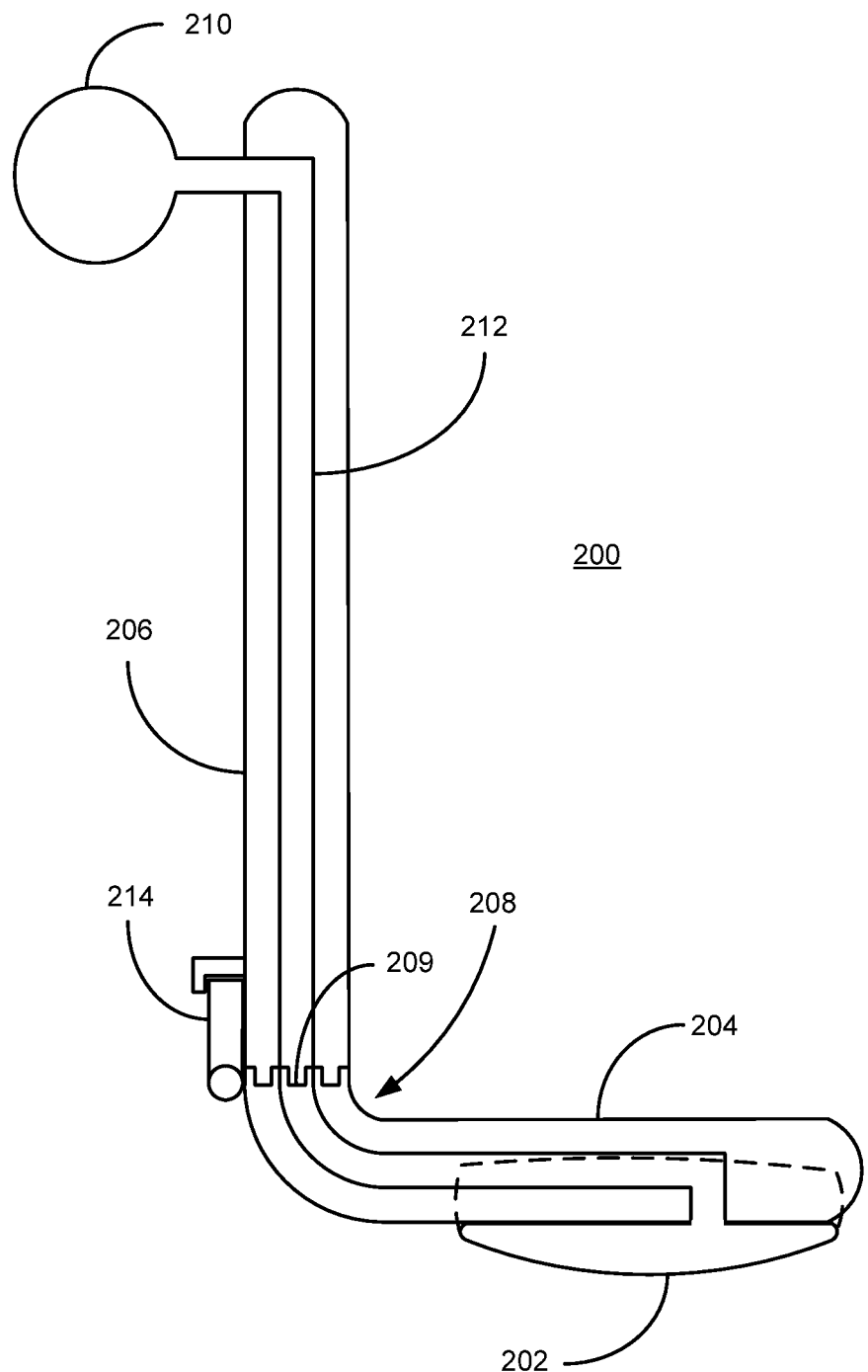
FIG. 2 depicts an embodiment of a rectocele device adapted to mechanically reduce the bulge of the rectocele during a bowel movement, consistent with embodiments of the present invention.

Consistent with embodiments of the present invention, FIG. 2 depicts an embodiment of a rectocele device 200 adapted to mechanically reduce the bulge of the rectocele 104 during a bowel movement. More specifically, the rectocele device 200 generally comprises a handle 206 that is integrated with a paddle 204 whereby the paddle 204 and the handle 206 are distinguished by a bend 208 in the rectocele device 200. In other words, the paddle 204 is essentially defined at the bend location 208 in the rectocele device 200. In the present illustrative embodiment, the rectocele device 200 is essentially an L-shaped unit (bend at 90 degrees) comprising the paddle 204 and the handle 206, though other embodiments contemplate a bend different from 90 degrees. An expandable sheath 202 is located on the paddle 204 and, in one embodiment, is expanded by an inflation means that expands a uniform sheath 202 into a non-uniform shape. In the present embodiment, the expandable sheath 202 is contemplated to be made out of silicone (or some other stretchable material). Other embodiments contemplate a mechanical expansion mechanism to expand the expandable sheath 202. In the depicted embodiment, the expandable sheath 202 is essentially inflated via a balloon catheter system disposed inside of the expandable sheath 202, which is inflated by compressing an inflation bulb 210 located at or near the end of the handle 206. Air, or some other comparable fluid or gel able to accomplish similar effects, flows through a tube 212 that is connected to the expandable sheath 202 and the inflation bulb 210. In this embodiment, the expansion sheath 202, the inflation bulb 210 and the tube 212 essentially maintain a constant volume of air, or comparable fluid, such that when the inflation bulb 210 is squeezed, the expandable sheath 202 expands. Other inflation means contemplated include a spring loaded push-button system that is finger activated (not shown), whereby a finger pushes down on a vertical rod that depresses the inflation bulb 210, filling a balloon in the expandable sheath 202 with air, thus expanding the expandable sheath 202. Yet another embodiment contemplates a compressed air cartridge, such as a $CO_2$ cartridge, that can be activated, such as by a push button, to inflate the expandable sheath 202 with a release valve to decompress the expandable sheath 202. Other embodiments contemplate an electrically powered pump inflating a balloon that expands the expandable sheath 202. The preceding embodiments for inflating a balloon disposed inside of the expandable sheath 202 are by way of example and are not limiting to the optional means of inflation within the scope and spirit of the present invention. Hence, there are a variety of ways to expand the expandable sheath 202, which are within possession and knowledge of a skilled artisan.

Certain embodiments contemplate the rectocele device 200 being used essentially from just prior to a bowel movement of a woman to just after the bowel movement of the woman. By using the rectocele device 200 for essentially just a bowel movement, a woman can live free from a foreign object in her vagina 106 during her normal daily activities. Hence, when a woman needs to move stool, she inserts the paddle 204 in her vagina 106 and expands the expandable sheath 202, such as, for example, by squeezing the air out of the inflation bulb 210. The expandable sheath when expanded is in contact with the woman's rectovaginal wall 102. During operation, the handle 206 remains outside of the vagina 106 at essentially where the bend 208 is located. The handle 206 translates directional pressure on the rectovaginal wall 102 by way of the paddle 204 when the handle 206 is in manually pulled towards the woman's belly button 116. More specifically, the handle 206 is used as a lever rotating about the mons veneris 120, thus pushing back the rectocele 104 by way of the paddle 204 and expandable sheath 202 pushing against the rectovaginal wall 102. When the woman has completed moving stool, she contracts the expandable sheath 202, such as, for example, by releasing the inflation bulb 210, and withdraws the paddle 204 from her vagina 106.

Certain embodiments contemplate the expandable sheath 202 being in contact with the rectovaginal wall 102 and lateral walls (not shown) of the vagina 106, but not in contact with the bladdervaginal wall 110. By being in contact with the at least a portion of the lateral walls of the vagina 106 and the rectovaginal wall 102, the expandable sheath 202 helps control the rectocele 104 from sliding around the side of (to the right or left) the paddle 204. Accordingly, the rectocele 104 is adequately compressed to allow the stool to evacuate effectively with the rectocele device 200.

Also, depicted in FIG. 2 is an embodiment where the paddle 204 is removable from the handle 206 via a joint 209.

Advantages of the paddle 204 being removed from the handle 206 includes the option for a disposable paddle 204, or a paddle 204 that is potentially more easily cleaned. The paddle 204 can be removed from the handle 206 via a latching mechanism 214, shown herein. The joint 209 and latching mechanism 214 are an embodiment illustrating a removable paddle 204 and is not intended to be limiting to optional ways to accomplish providing a removable paddle 204 within the scope and spirit of the present invention.

Figure 3:
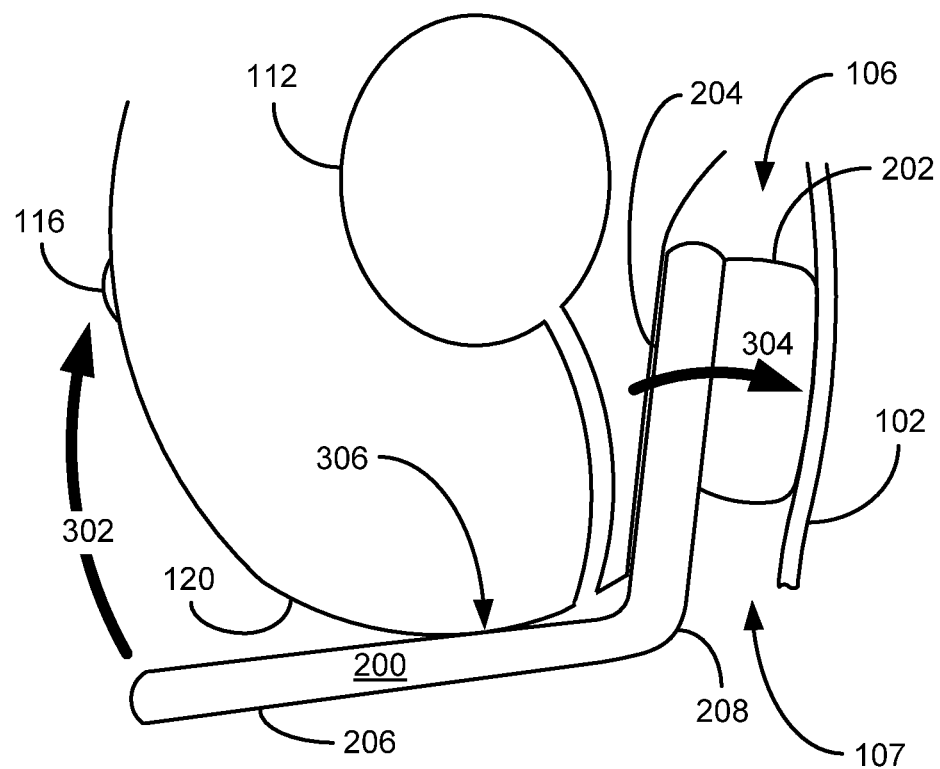
FIG. 3 depicts a rectocele device being used to press against a rectocele, consistent with embodiments of the present invention.

FIG. 3 depicts a rectocele device 200, consistent with embodiments of the present invention, being used to press against a rectocele 104. As illustratively shown, the paddle 204 is located in the vagina 106 and the expandable sheath 202 is expanded and pressing against the rectovaginal wall 102 in the direction shown by arrow 304. The handle 206 is being pulled towards the belly button 116 as indicated by the arrow 302, which pivots the rectocele device 200 about the pivot point 306 on the mons veneris 120. As shown, the bend 208 is essentially outside of the vaginal opening 107. Also, in this embodiment, the expandable sheath 202 does not contact the bladdervaginal wall 110. However, optional embodiments contemplate an expandable sheath additionally contacting the bladdervaginal wall 110.

Figure 4:
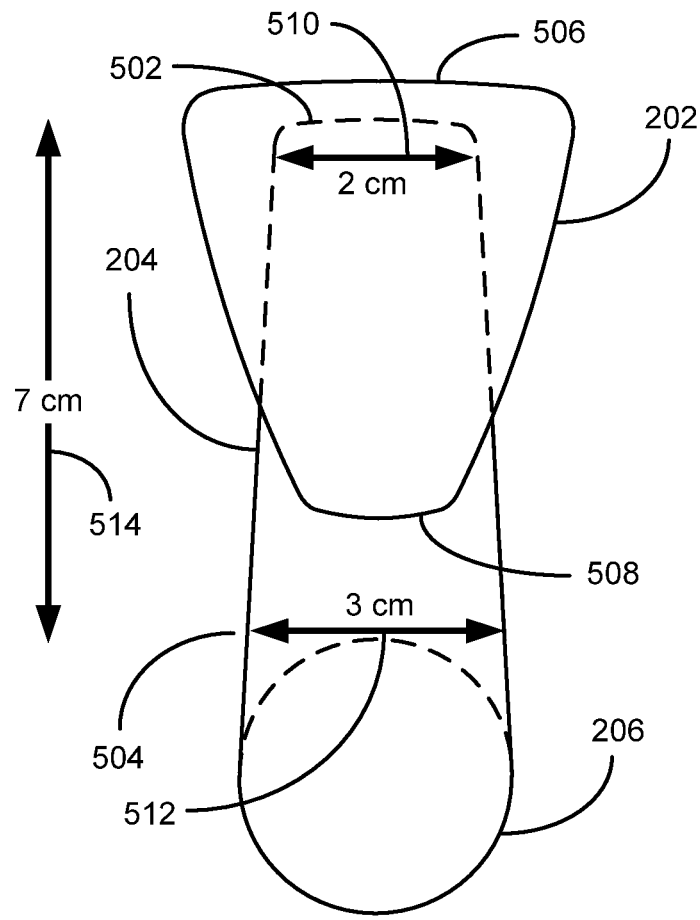
FIG. 4 illustratively shows a view of the expandable sheath that contacts the rectovaginal wall when expanded, consistent with embodiments of the present invention.

FIG. 4 shows a view of the expandable sheath 202 that contacts the rectovaginal wall 102 when expanded. As illustratively shown, the present embodiment depicts the expandable sheath 202 possessing a non-uniform shape when expanded. More specifically, the expandable sheath 202 possesses a wide top end 506 and a narrow bottom end 508 because the vaginal vault 106 naturally accommodates this shape well. Also as illustratively shown, the paddle 204 is tapered such that the top end 502 is narrower than the paddle bottom end 504 to improve insertion into the vagina 106. One embodiment contemplates the paddle top end 502 to be approximately 2 cm in width and the bottom to be approximately 3 cm in width. Certain embodiments further contemplate the paddle length to be between 4 cm and 9 cm in length, but preferably 7.5 cm in length.

Figure 5:
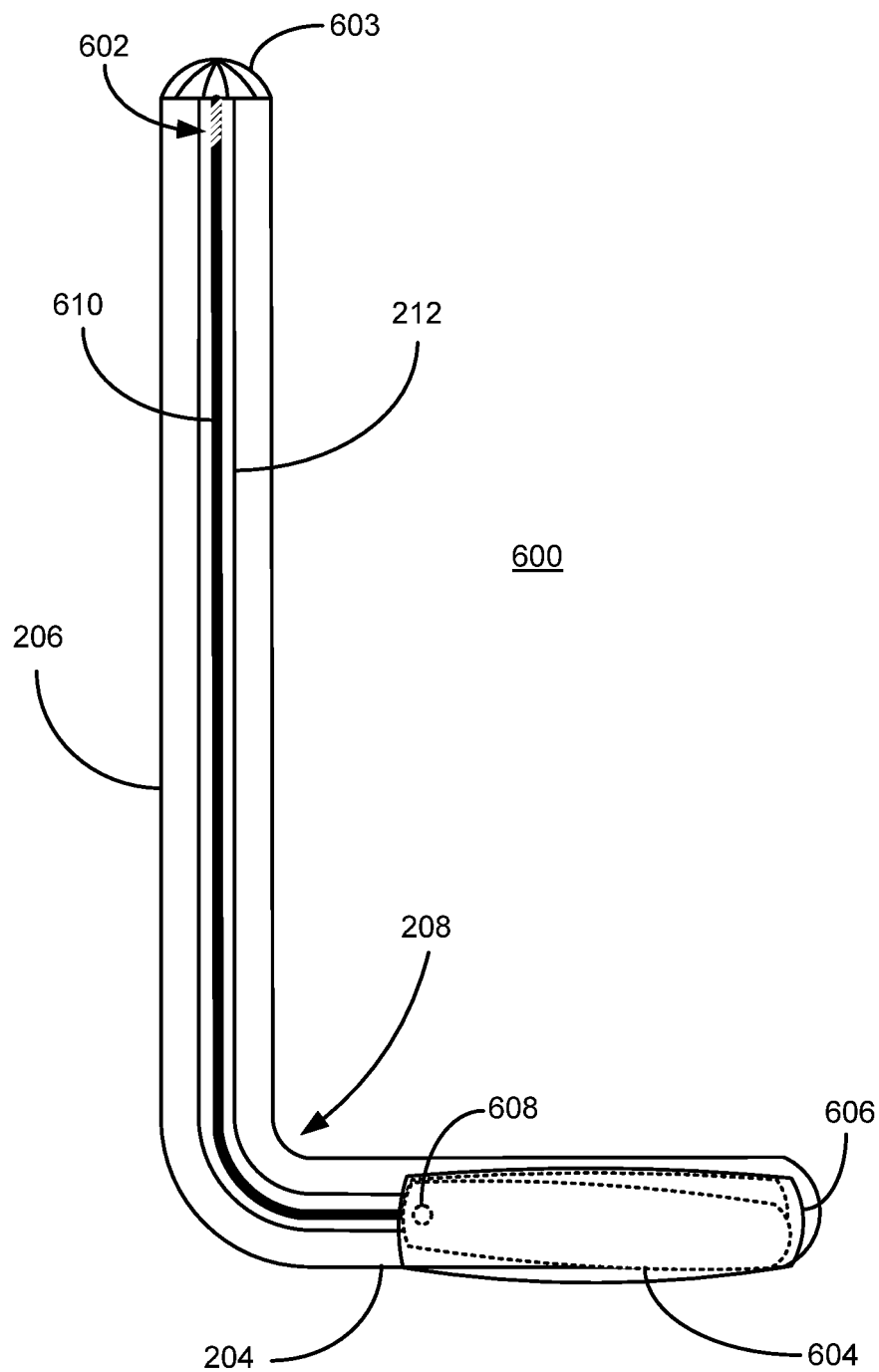
FIG. 5 shows an optional embodiment of an expandable sheath that is expanded by a mechanical hardware, consistent with embodiments of the present invention.
Figure 6A:
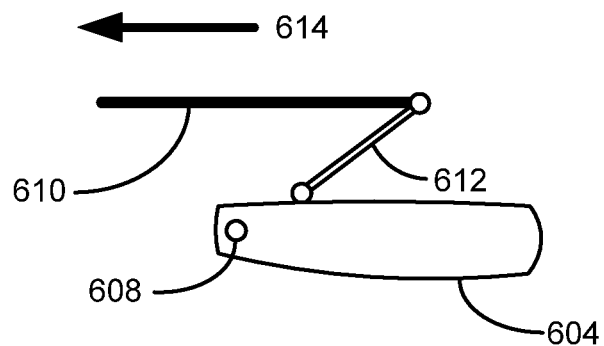
Figure 6B:
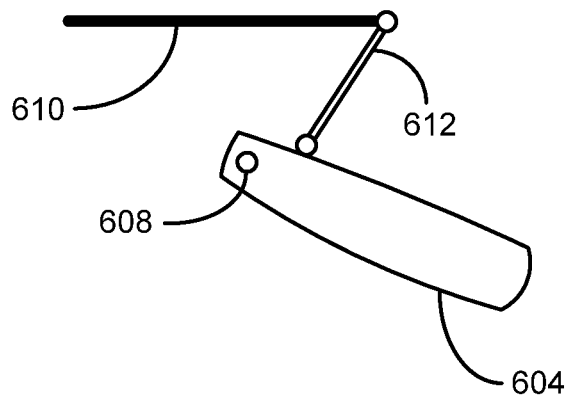

FIG. 5, as shown in conjunction with FIGS. 6A-6D, shows an optional embodiment wherein the expandable sheath 606 is expanded by mechanical hardware, consistent with embodiments of the present invention. With reference to FIG. 5, the expandable sheath 606 is disposed on the paddle 204 of the rectocele device 600. Here, the uniform shaped sheath 606 is not expanded. Contained inside the expandable sheath 606 is hardware, such as blades 604 that may be mechanically expanded by way of a knob 603 located at the end of the handle 206. In conjunction with FIGS. 6A and 6B, as the knob 603 is rotated, a threaded end 602 of a flexible rod 610 coupled with a captured bolt (not shown) in the knob 603 pulls the flexible rod 610 into the knob 603, directionally shown by arrow 614, which directionally rotates the blade about a pivot point 608 via a linking arm 612, for example. In this way, the blades 604 move from a retracted position, shown in FIG. 6C, to an expanded position, shown in FIG. 6D, thus expanding the sheath 606 as shown. It should be appreciated that the illustrated embodiment of the mechanically expanding sheath is by way of example and is not limiting to other engineering designs to mechanically accomplish expanding the flexible sheath 606 within the scope and spirit of the present invention.

FIGS. 7A and 7B depict an alternative embodiment of a rectocele device 700, consistent with embodiments of the present invention. As illustratively shown in FIG. 7B, the paddle 204 possesses an expandable sheath 702 that essentially expands around the circumference of the paddle 204, which when inserted and expanded in a vagina 106 contacts the rectovaginal wall 102, the bladdervaginal wall 110 and the lateral vaginal walls of the vagina. FIG. 7A illustratively shows that the expandable sheath 702 is in a non-expanded state whereby the inflation bulb 210 is expanded. FIG. 7B illustratively shows the expandable sheath 702 is in an expanded state whereby the inflation bulb 210 is compressed.

Figure 8:
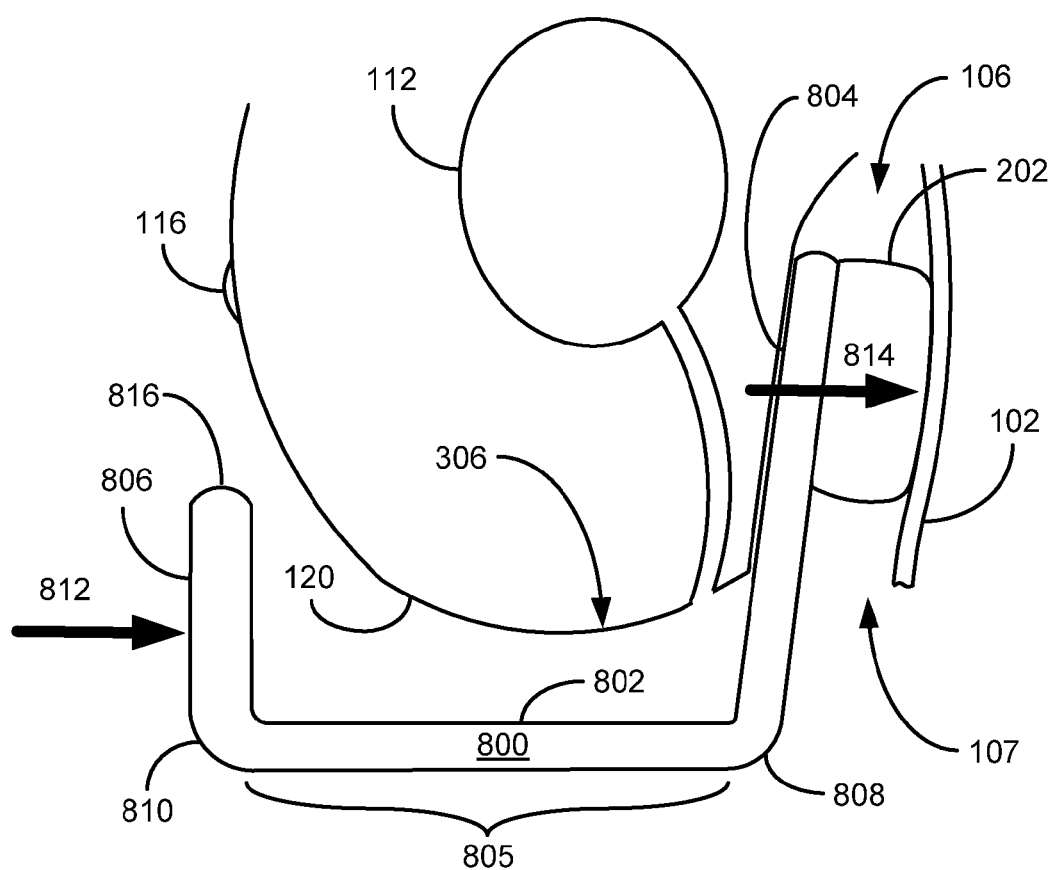
FIG. 8 depicts yet another alternative embodiment of a rectocele device, consistent with the present invention.

FIG. 8 depicts yet another alternative embodiment of a rectocele device 800, consistent with the present invention. As illustratively shown, the paddle 804 is located in the vagina 106 and the expandable sheath 202 is expanded and pressing against the rectovaginal wall 102 in the direction shown by arrow 814. The handle 802 is defined from the paddle 804 by a first bend 808, which is just outside of the vaginal opening 107. The handle 802 further comprises a grip 806 which is defined by a second bend 810 and the distal end of the handle 816. For reference, the handle 802 possesses a mid-handle portion 805 between the first bend 808 and the second bend 810. In this embodiment, when the grip 806 is pressed towards the posterior direction 812, the expandable sheath 202 operably pushes (arrow 814) against the rectovaginal wall 102, thus addressing the rectocele 104. Though one embodiment contemplates the first bend 808 being essentially 90 degrees between the mid-handle portion 805 and the paddle 804 and the second bend 810 being essentially 90 degrees between the mid-handle portion 805 and the grip 806, other embodiments contemplate the bends 808 and 810 being different angles greater than 45 degrees and less than 135 degrees for example.

Figure 9:
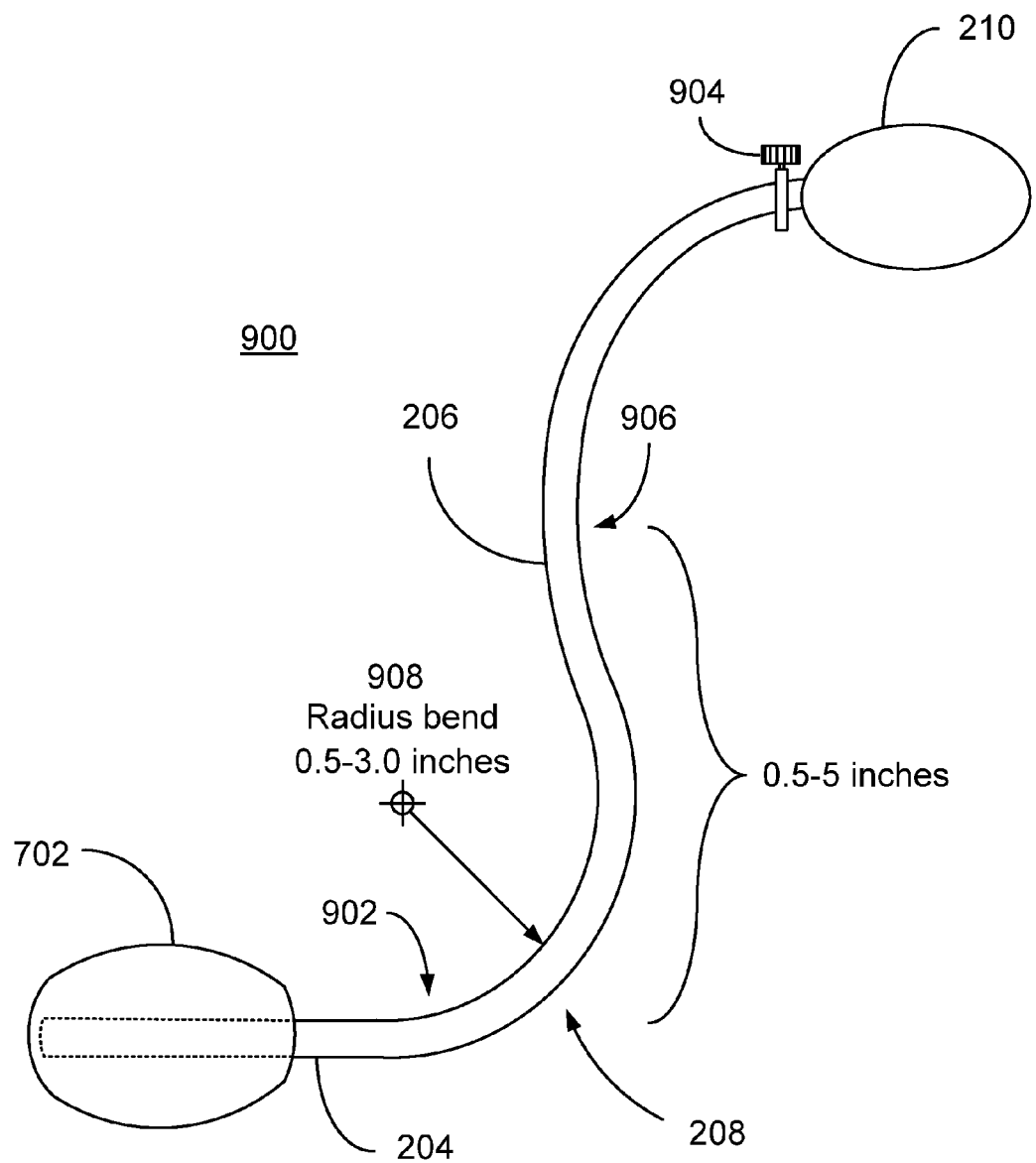
FIG. 9 depicts a rectocele/cystocele device embodiment in accordance with embodiments of the present invention.

FIG. 9 depicts an embodiment of rectocele/cystocele device 900 consistent with embodiments of the present invention. As illustratively shown, the paddle 204 and the handle 206 are defined by the bend 208 in the device 900, which starts at the bend starting point 902 essentially forming an L-shaped unit. Some embodiments contemplate the bend 208 not being capable of passing into the vaginal opening 107, while other embodiments contemplate just a small portion of the bend 208 being able to pass into the vaginal opening 107. The bend 208 possesses a radius 908 that is in the range between 0.5 inches and 3.0 inches. The handle 206 is shown curving away from the paddle 204 in an "S" shaped configuration wherein the length of the bend 208 extends from the bend starting point 902 to the bend ending point 906. Some embodiments contemplate the bend starting point 902 to the bend ending point 906 being in the range of between 0.5 inches and 5.0 inches long. The rectocele/cystocele device 900 also comprises an expandable sheath 702 located on the paddle 204 that after being inserted in a woman's vagina 106 is expanded therein to contact at least the start of the cervix 1006 and the rectouterine pouch 1012, also essentially the posterior fornix region 1071, of the vagina 106 (see FIG. 10). In the case where there is a hysterectomy and the cervix 1006 is not present, contact is made with the posterior fornix region 1071. The handle 206, which does not go into the vagina 106, is adapted to be manipulated by a woman 100 to translate directional pressure against the pelvic floor 1008 via the expandable sheath 702 when the expandable sheath 702 is expanded (via the inflation bulb 210, used herein for example, or other previously disclosed ways to expand the expandable sheath 702). This action will adjust the position of the cervix 1006 and the rectouterine pouch 1012 of the vagina 106, thus supporting the pelvic floor in a direction suitable for defecating or urinating comfortably. In an optional embodiment, the expandable sheath 702 is manipulated by the handle 206 to lift the rectouterine pouch 1012 in a direction away from the vaginal opening 107 when the handle 1004 is in manually manipulated by the woman 100. Certain embodiments contemplate the expandable sheath 702 expanded to a size large enough to "smooth out" bulges that may intrude on the vaginal wall 103 such as by the bladder or rectal regions, for example. Also, depicted in FIG. 9 is a release valve 904 located near the inflation bulb 210 that when turned appropriately allows for deflating the expandable sheath 702.

Figure 10:
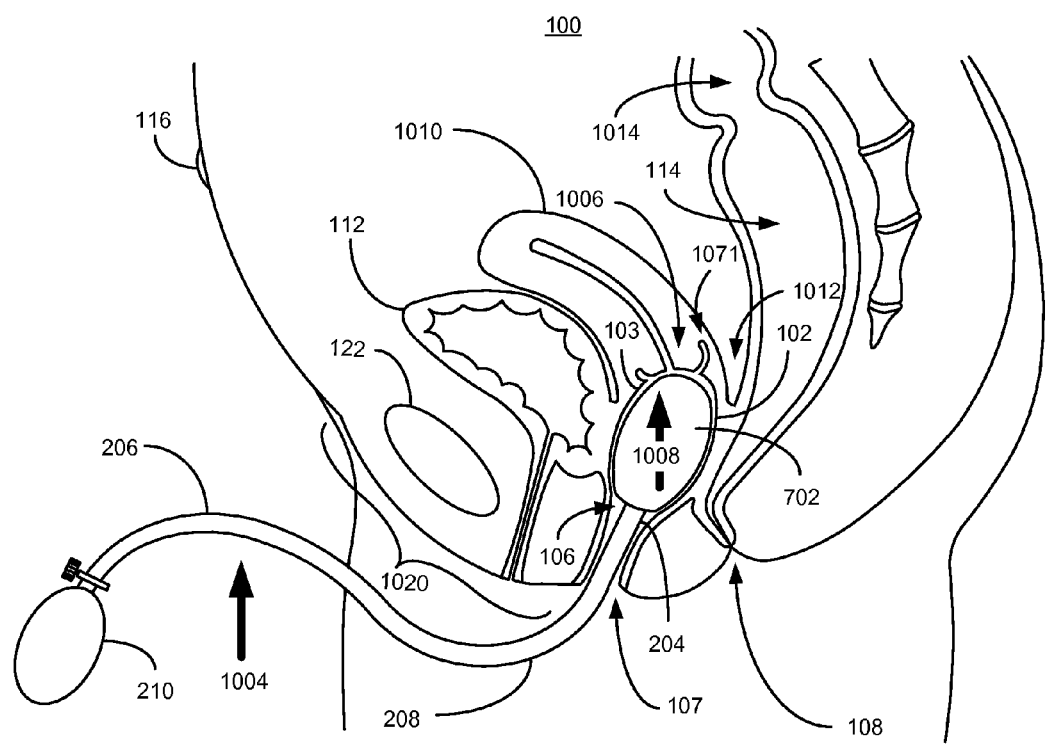
FIG. 10 depicts a rectocele/cystocele device in use with a woman in accordance with embodiments of the present invention.

As depicted in FIG. 10, the expanded sheath 700, can essentially occupy a significant portion of vaginal cavity 106 (shown here to occupy approximately 50% of the vaginal cavity 106) providing support to the endopelvic fascia comprising the rectouterine pouch 1012 to reduce or eliminate pelvic organ prolapse of the anterior vaginal wall 110, the middle compartment (not shown) and the posterior vaginal wall 103. These types of prolapse are generally due to a weakening in the endopelvic fascial support system in the pelvic floor (due to old age or childbirth). The endovaginal fascia supports the bladder 112, vagina 106, uterus 1010, rectum 114 and sigmoid colon 1014 and is involved in bladder storage, voiding and continence, for example. They are also involved in providing support for the vaginal wall 103, cervix 1006 and uterus 1010. They have a major role in defecation and continence of feces. Abnormalities of the pelvic floor, which generally comprise the muscles and ligaments that support the organs in the pelvis, manifest themselves as urinary incontinence, uterovaginal prolapse (uterine prolapse), sexual dysfunction, obstructed defecation and fecal incontinence. The handle 206 and paddle 204 of the rectocele/cystocele device 900 are adapted to adjust the cervix 1006, the rectouterine pouch 1012, and vaginal wall 103 generally by lifting the those regions into a more natural position (originally supported by the pelvic floor muscles) to reduce the aforementioned abnormalities. Lifting the pelvic organs into a natural position helps reduce urinary incontinence, uterovaginal prolapse, obstructed defecation and fecal incontinence during the lifted period. Because the paddle 204 is inserted through the vaginal opening 107 into the vagina 106 just prior to a bowel movement (or urination), such as within five minutes, there is only temporary relief for defecating and urinating.

With further reference to the rectocele/cystocele device 900, the bend 208 possesses a bend radius 908 that provides clearance around the pelvic region 1030. This clearance makes it possible to avoid contacting the handle 206 with the pelvic region 1030, thus facilitating freedom without obstruction to adjust the expandable sheath 702 upwards, from side to side, posterior, anterior, etc., to improve urinating or defecating. As depicted, the handle 206 is manipulated towards the woman's belly button 116 in an upwards direction 1004, thus translating the pressure directionally upwards 1008 against the cervix 1006, rectouterine pouch 1012, and vaginal wall 103 via the expandable sheath 702 when expanded. Optional embodiments contemplate a small radial bend 208 between the handle 206 and the paddle 204 wherein the paddle 204 is sufficiently long enough to accomplish the same goal of providing enough clearance between the handle and the pelvic region 1030 to avoid contact during use.

Figure 11:
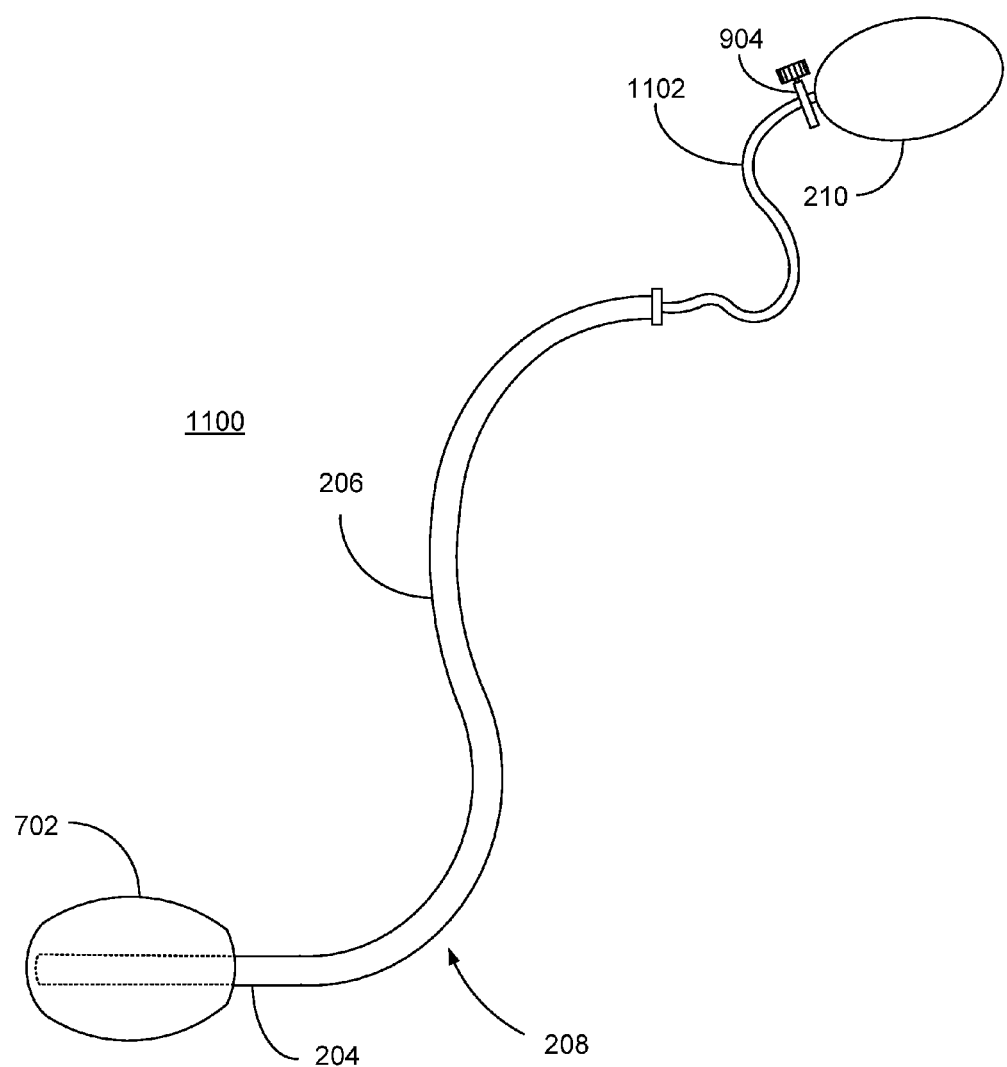
FIG. 11 depicts another embodiment of a rectocele/cystocele device in accordance with embodiments of the present invention.

FIG. 11 is an optional embodiment of a rectocele/cystocele device 1100 consistent with embodiments of the present invention. As depicted, the inflation bulb 210 is attached to a flexible line 1103 to provide more freedom to operate for the end user (woman). Together with the handle 206 and paddle 204, the flexible line 1103 maintains a continuous pathway between the inflation bulb 210 and the expandable sheath 702.

Figure 12:
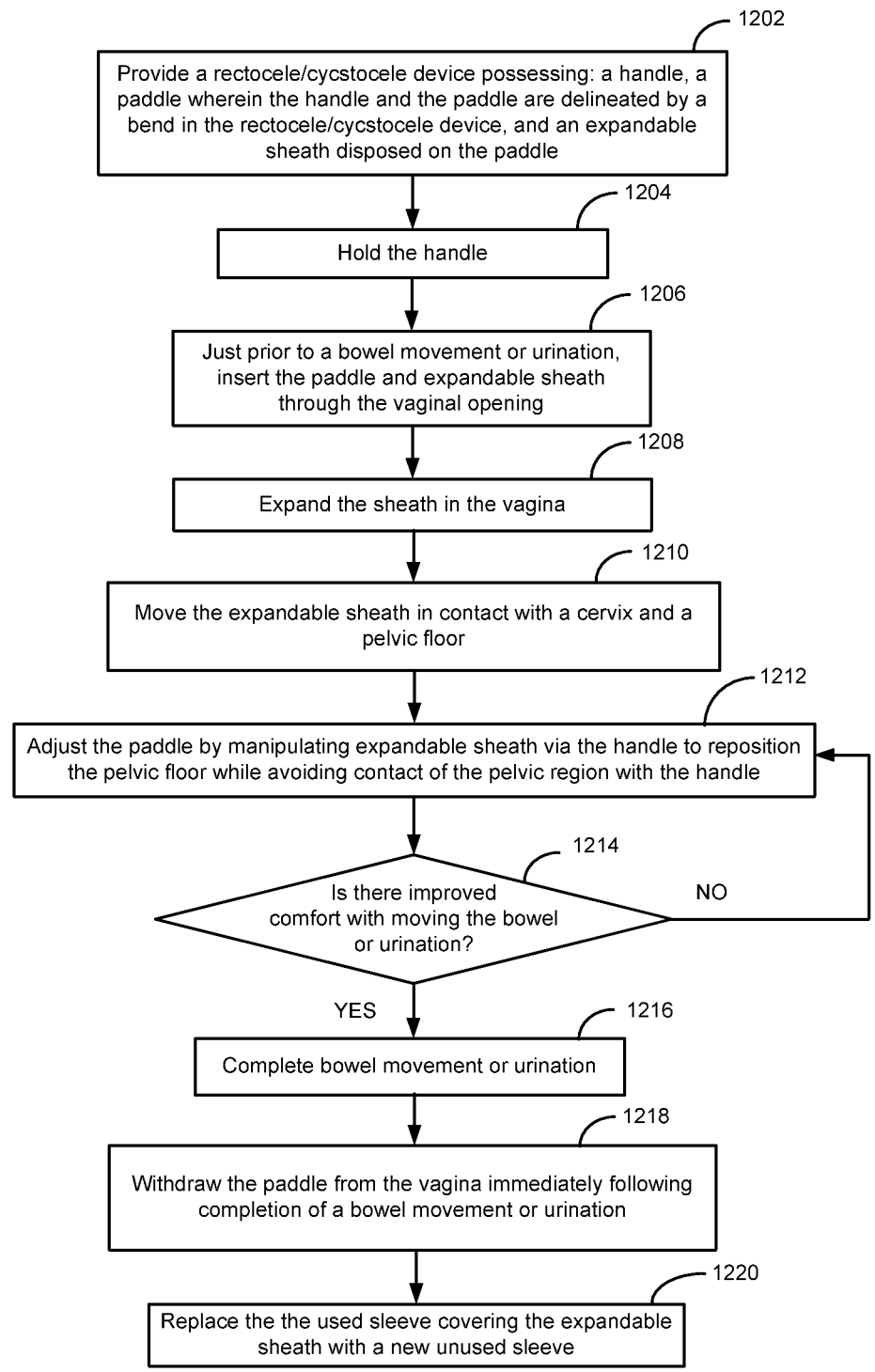
FIG. 12 depicts a method to ease a defecation event or a urination event in a woman consistent with embodiments of the present invention.

FIG. 12, in conjunction with FIG. 10, illustrates method steps to ease defecation events or urination events in a woman who solely performs the method on herself using a rectocele/cystocele device consistent with embodiments of the present invention. As shown in step 1202, a rectocele/cystocele device 900 is provided with a handle 206, a paddle 204 wherein the handle 206 and the paddle 204 are delineated by a bend 208 in the rectocele/cystocele device 900. The rectocele/cystocele device 900 further possesses an expandable sheath 702 disposed on the paddle 204. As illustrated by step 1204, when the woman 100 feels the need to either urinate or defecate, the woman 100, while holding the rectocele/cystocele device 900 by the handle 206, inserts the paddle 204 and expandable sheath 702 through her vaginal opening 107 just prior to urinating or defecating. The handle 206 remains outside of her vaginal opening 107, step 1206. Once the expandable sheath 702 is in the vagina 106, the woman 100 inflates the expandable sheath 702 by manually squeezing the inflation bulb 210, step 1208. The expandable sheath 702 is then moved away from the vaginal opening 107 until the expandable sheath 702 is in contact with the cervix 1006, rectouterine pouch 1012, and vaginal wall 103, step 1210. Once in contact, the expandable sheath 702 can be manipulated by the handle 206 to adjust the pelvic floor 702 in a second position, such as a lifted position, wherein the handle 206 avoids contact with the pelvic region 1020, step 1212. Step 1214 is a decision block whereby the woman 100 senses whether or not there is an improvement in her comfort in defecating or urinating. If her comfort is not improved, go back to step 1212 and keep adjusting the cervix 1006, rectouterine pouch 1012, and vaginal wall 103 with the expandable sheath 702 until her comfort level is improved enough to complete the bowel movement or urination, step 1216. Once finished with defecating or urinating, the woman 100 can deflate the expandable sheath 702 by opening the release valve 904 and withdraw the paddle 204 from the vagina 106, step 1218. Deflating the expandable sheath 702 does not need to occur prior to removing the expandable sheath 702 from the vagina 106. In an optional embodiment, where the expandable sheath 702 has a sleeve 1302 covering it, the sleeve 1302 can be removed after each use and a new sleeve 1302 can be disposed to cover the expandable sheath 702. Each use is considered when the sleeve 1302 is over the expandable sheath 702 and in the vagina 106 during one defecation or urination event.

Figure 13A:
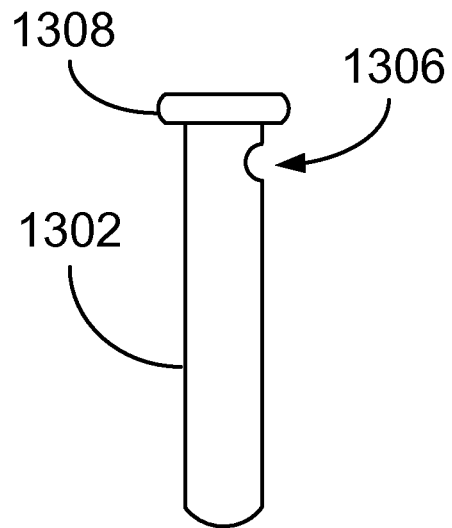
FIGS. 13A-13F depict embodiments of a sleeve used to cover the expandable sheath consistent with embodiments of the present invention.
Figure 13B:
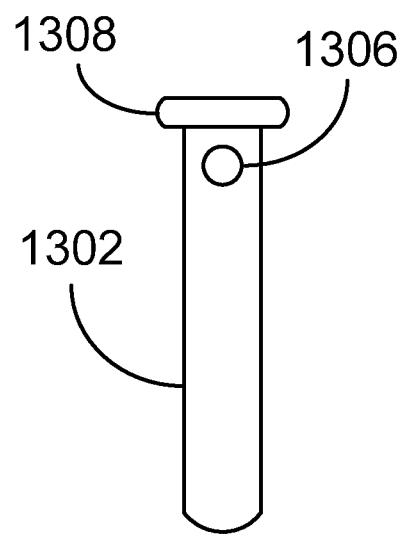
Figure 13C:
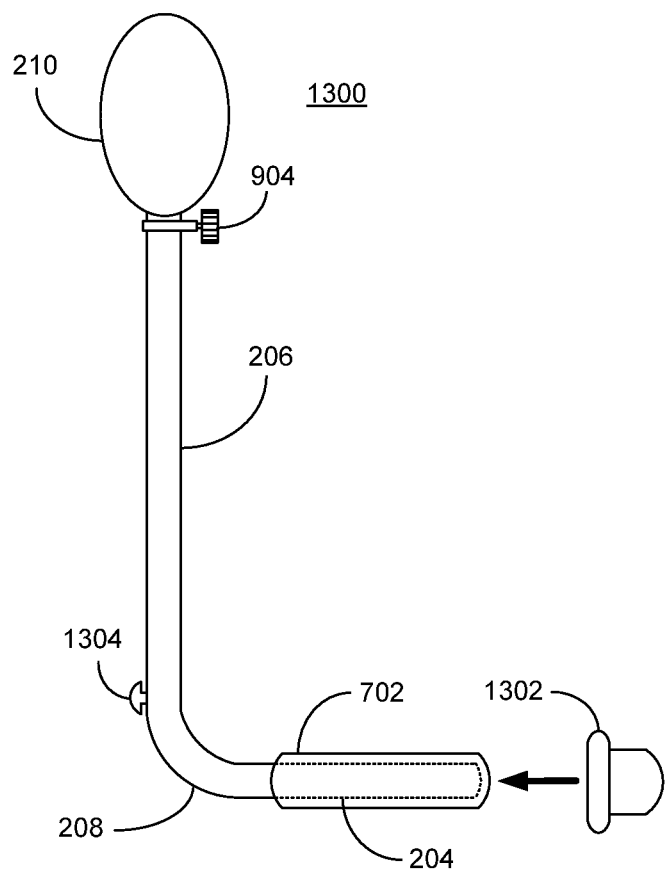
Figure 13D:
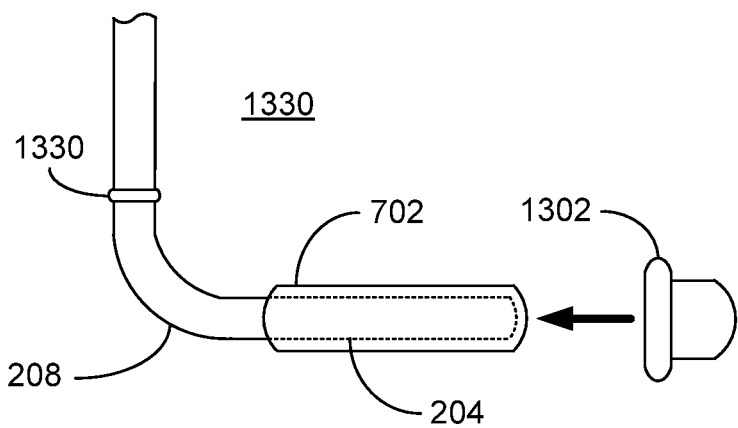
Figure 13E:
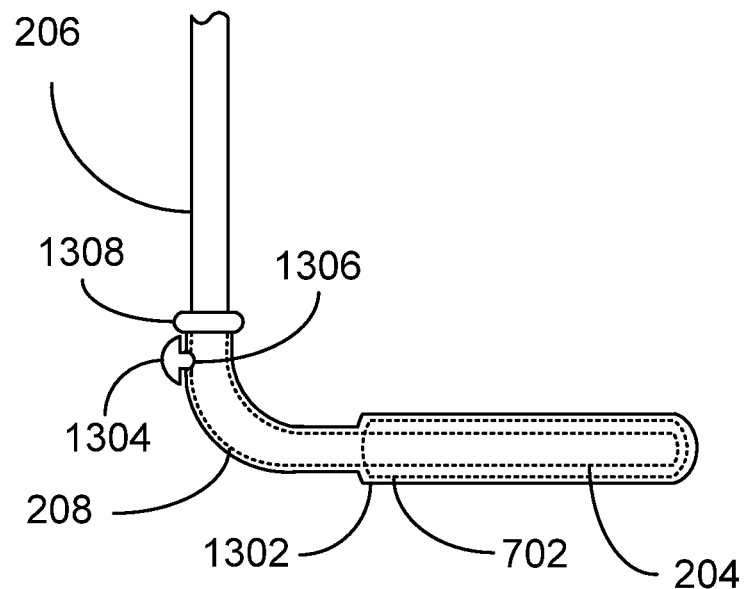
Figure 13F:
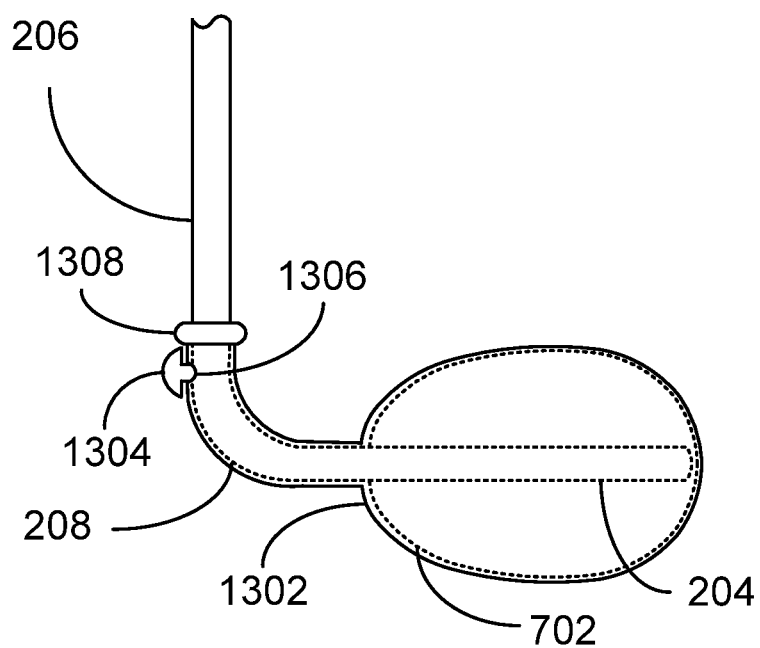

FIGS. 13A-13E illustratively depict various embodiments of a flexible replaceable sleeve 1302 covering an expandable sheath 702 consistent with embodiments of the present invention. The replaceable sleeve 1302 is adapted to cover the expandable sheath 702 and act as a barrier to prevent contact between the expandable sheath 702 and the vagina 106. The replaceable sleeve 1302 is adapted to be flexible, like a balloon, to freely expand and contract with the expandable sheath 702. Accordingly, the replaceable sleeve 1302 can be made from latex, rubber, or some other elastomeric polymer. In one embodiment, the replaceable sleeve 1302 is contemplated to be rolled up like a condom with a rubber band 1308 near the opening and unrolled over the expandable sheath 702 and paddle 204. Yet another embodiment contemplates the replaceable sleeve 1302 possessing a button hole 1306 where through a button 1304 (located on the rectocele/cystocele device 1300) can fix the replaceable sleeve 1302 in place. FIGS. 13E and 13F illustratively depict the replaceable sleeve 1302 over the expandable sheath 702 when not expanded and when expanded. Yet another embodiment contemplates the rectocele/cystocele device 1330 comprising a circular lip 1332 that goes around the circumference of the paddle 204, bend 208 or handle 206 (see FIG. 13D). The replaceable sleeve 1302, possessing a rubber band 1308, snaps over the circular lip 1332 and is fixed in place until removed. Another embodiment contemplates that the inner circumference of the replaceable sleeve 1302 and rubber band 1308 is smaller than the circumference of the paddle 204, bend 208 or handle 206 whereby the friction between the replaceable sleeve 1302 and the rectocele/cystocele device is enough to hold the replaceable sleeve 1302 in place during use. Optionally, the replaceable sleeve 1302 possesses a lubricant on the outside that when rolled over the expandable sheath 702 provides easy penetration of the paddle 204 into the vagina 106.

Figure 1B:
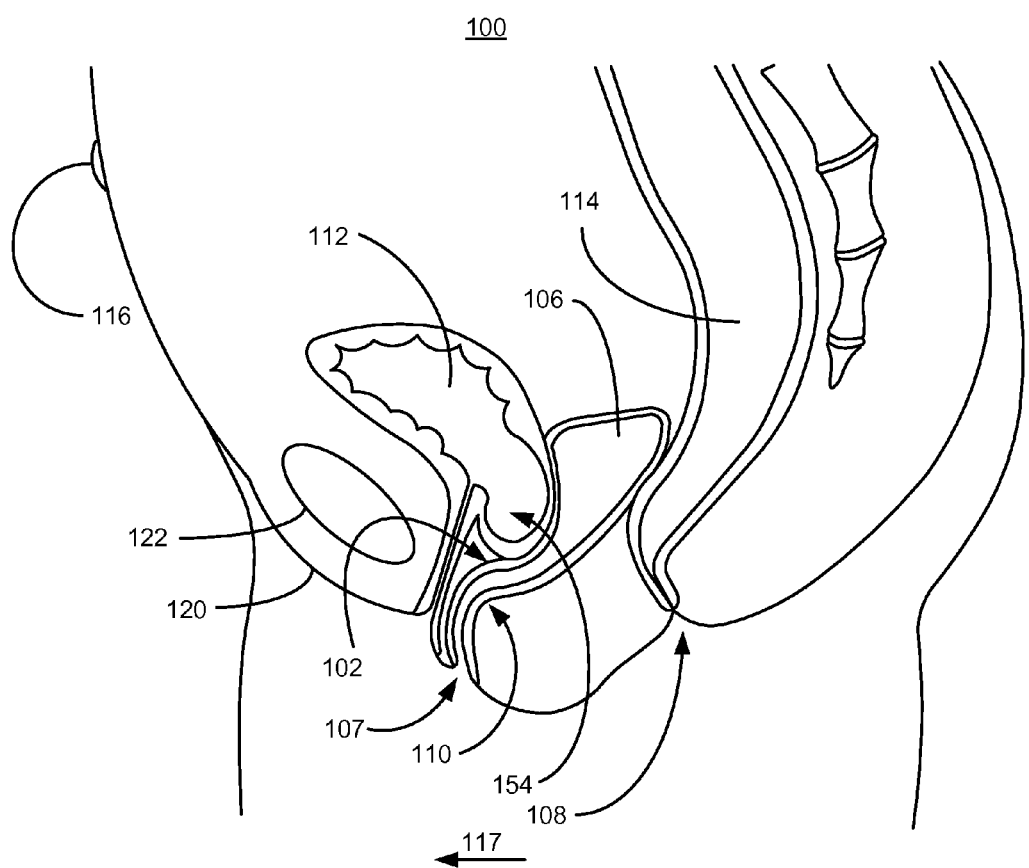
FIG. 1B depicts a cross section of a pelvic area of a woman suffering from a cystocele.
Figure 14:
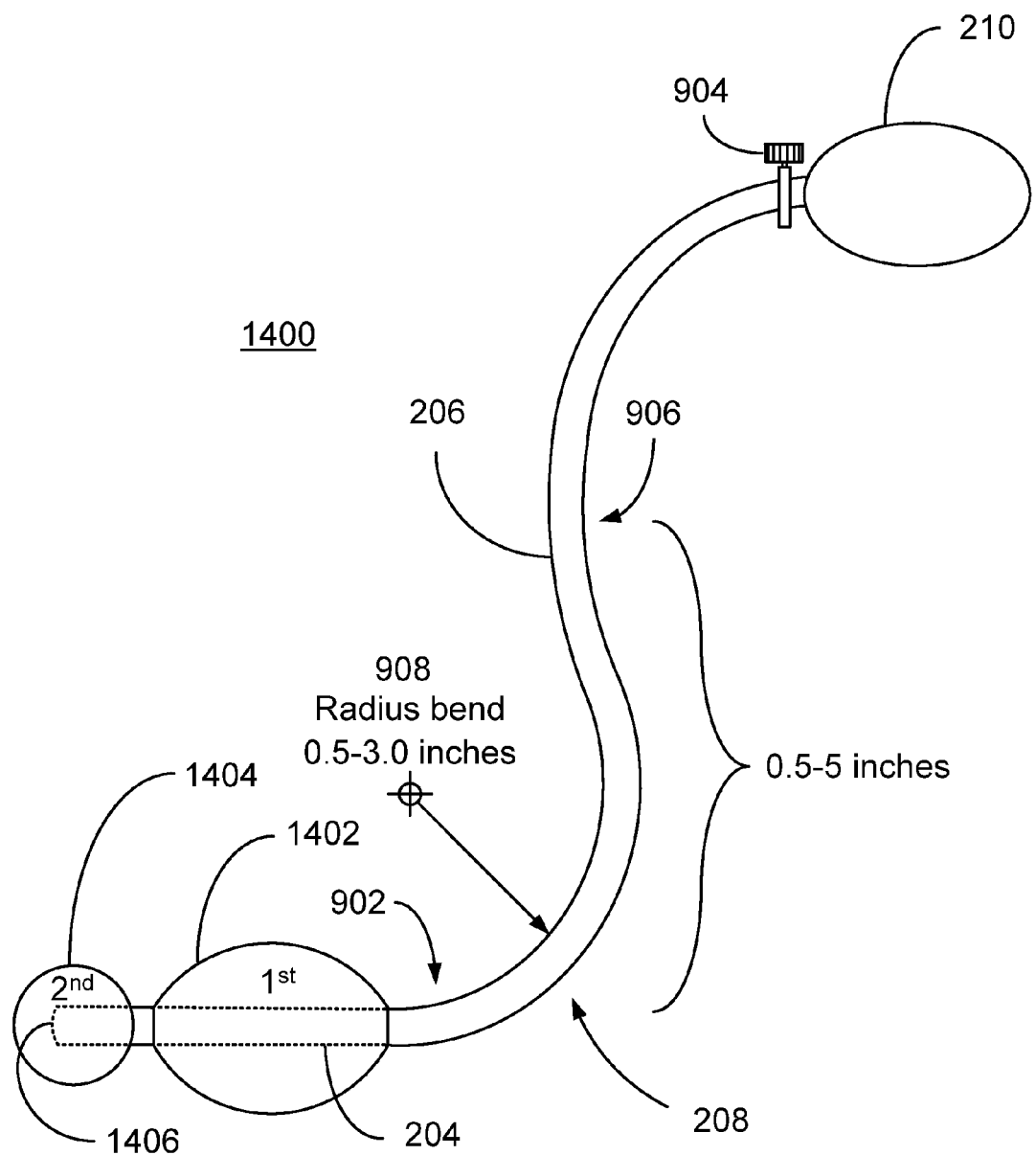
FIG. 14 depicts a recto-cystocele device embodiment comprising two balloons consistent with embodiments of the present invention.

FIG. 14 illustratively depicts yet another embodiment of a recto-cystocele device 1400 comprising two balloons consistent with embodiments of the present invention. As shown, the recto-cystocele device 1400 comprises an expandable sheath possessing a first balloon portion 1402 that is disposed on the paddle 204 between the bend 902 and the distal end 1406 of the paddle 204 and a second balloon portion 1404 that is disposed on the paddle 204 and extends beyond the distal end 1406 of the paddle 204. Here, the second balloon portion 1404 after being inserted in the woman's vagina 106 and inflated is in contact with at least an upper portion of the vagina 106 that includes the posterior fornix region 1071 of the vagina 106. In a woman 100 that has not had a hysterectomy; the second balloon portion 1404 is intended to be in contact with the woman's cervix 1006 when inflated, which includes the posterior fornix region 1071. Hence, certain appropriate manipulation of the second balloon 1404 provides directional pressure upwards towards the uterus to help mitigate prolapse of the uterus and ease defecation, for example. Moreover, it is contemplated that the second balloon 1404 will further address Sigmoidocele (prolapsing sigmoid colon) and enterocele (prolapsing small intestine/small bowel). Sigmoidocele and enterocele will generally prolapse down into the rectum 114 and/or vagina 106 via the rectouterine pouch 1012. Occupying the space near the vaginal fornix 1071 (near cul de sac of the vagina) to prevent the sigmoid colon and/or small bowel from prolapsing down through the recto-uterine pouch 1012 and into the vagina 106 or rectum 114. Most patients will not have a prolapsing sigmoid, small bowel or uterus until they begin pushing during defecation. Certain embodiments contemplate using the second balloon 1404 being located in the cul de sac space 1071 area prior to pushing (a bowel movement) in order to essentially "dam" or occupy this area to prevent prolapse during defecation. Furthermore, aside from just occupying the cul de sac space 1071, the recto-cystocele device 1400 is adapted to apply directional pressure to the cul de sac space 1071 of the vagina and/or rectouterine pouch 1012 via the handle 206 to manually push back these prolapsing organs into a normal position for easier defecation. The first balloon portion 1402 after being inserted in the woman's vagina 106 is in contact with at least a middle portion of the vagina 106 that does not include the posterior fornix region 1071 of the vagina 106. The first balloon portion 1402 is intended to press against the side of the vagina 106 to push back a rectocele bulge 104 such as shown in FIG. 1A or a cystocele bulge 154 as shown in FIG. 1B. Fundamentally, the first and second balloon portions 1402 and 1404 in combination address the prolapse disorders discussed in conjunction with FIG. 10 by occupying the vaginal space where prolapse may occur.

Certain embodiments consistent with FIG. 14 contemplate the first balloon portion 1402 and the second balloon portion 1404 not overlapping. In other words, the first balloon portion 1402 and the second balloon portion 1404 inflate as independent balloons. Some embodiments contemplate the first balloon portion 1404 extending from beyond the bend 902 to no less than one half of an inch from the distal end 1406 of the paddle 204 and the second balloon portion 1404 extending at least one half of an inch beyond the distal end 1406 of the paddle 204.

Figure 15A:
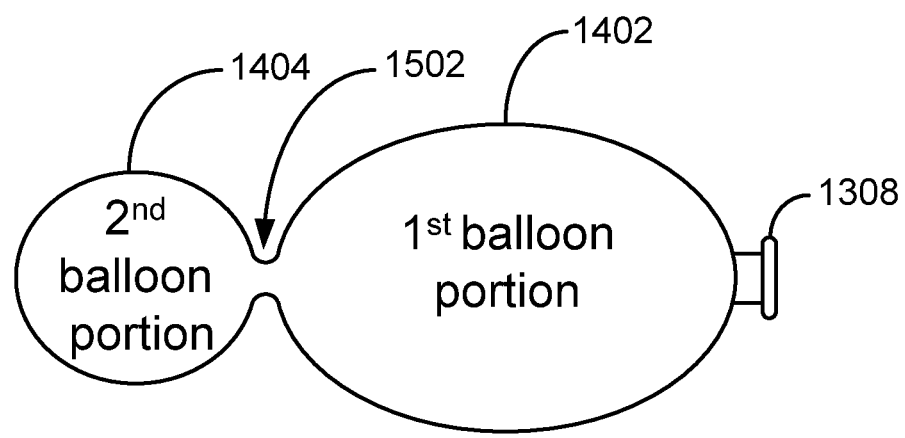
FIGS. 15A and 15B depict optional embodiments of a dual balloon expandable sheath consistent with embodiments of the present invention.
Figure 15B:
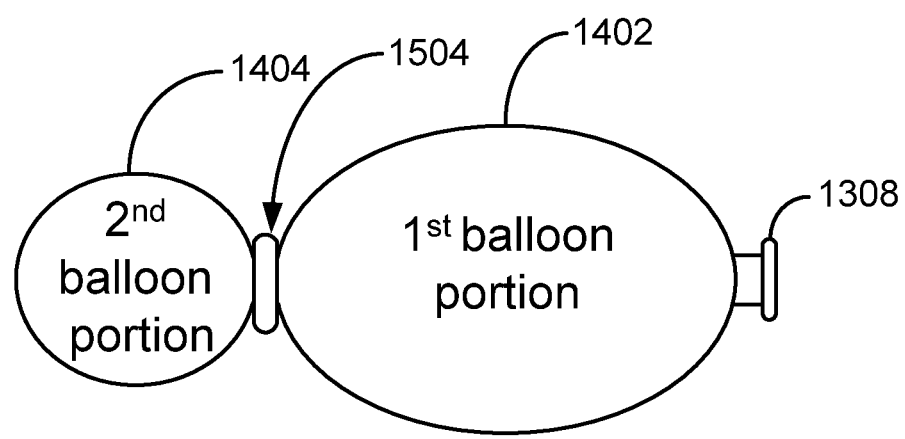

FIGS. 15A and 15B depict optional embodiments of a dual balloon expandable sheath consistent with embodiments of the present invention. As illustratively shown in FIG. 15A, one embodiment contemplates a separator 1502 that divides the first balloon portion 1402 from the second balloon portion 1404. The separator 1502 can be made and formed as an integral part of the sheath comprising the same material as the balloon portions 1402 and 1404. For example, if the balloons 1404 and 1402 are made from rubber or latex, then the separator 1502 is a thicker portion of rubber or latex. Some embodiments contemplate the separator 1502 comprised of an essentially non-expandable section that is capable of some flexibility to adjustably slide over the paddle 204 while maintaining separation between the balloons 1402 and 1404.

FIG. 15B depicts another embodiment of a separator 1504 that is essentially a rubber band that constricts air (or gel or other fluid) in the first balloon portion 1402 from moving into the second balloon portion 1404. The rubber band 1504 can be integrated with the sheath or can be "rolled over" the sheath (such as sheath 702 or over the sleeve 1302 from FIG. 13) once the sheath has been installed on the paddle 204. Other means for separating the first balloon portion 1402 from the second balloon portion 1404 are a matter of engineering design choices that a skilled artisan will appreciate fall within the scope and spirit of the present invention, after someone has been shown the inventive embodiments in the present description.

Further embodiments of the first balloon portion 1402 and the second balloon portion 1404 include independent sheaths. Other embodiments contemplate the first balloon portion 1402 and the second balloon portion 1404 possessing elastic material (rubber, for example) having different durameter stiffness. For example, the second balloon portion 1404 may be made of an elastic material with a higher durameter than the first balloon portion 1402. Optionally, the second balloon portion 1404 may be made of the same elastic material as the first balloon portion 1402, but only thicker thus creating a stiffer balloon (or vise-versa). Other embodiments contemplate more air pressure (fluid pressure) applied to the second balloon 1404 than the first balloon 1402. Yet other optional embodiments contemplate the first balloon portion 1402 never touching the second balloon portion 1404.

Figure 16:
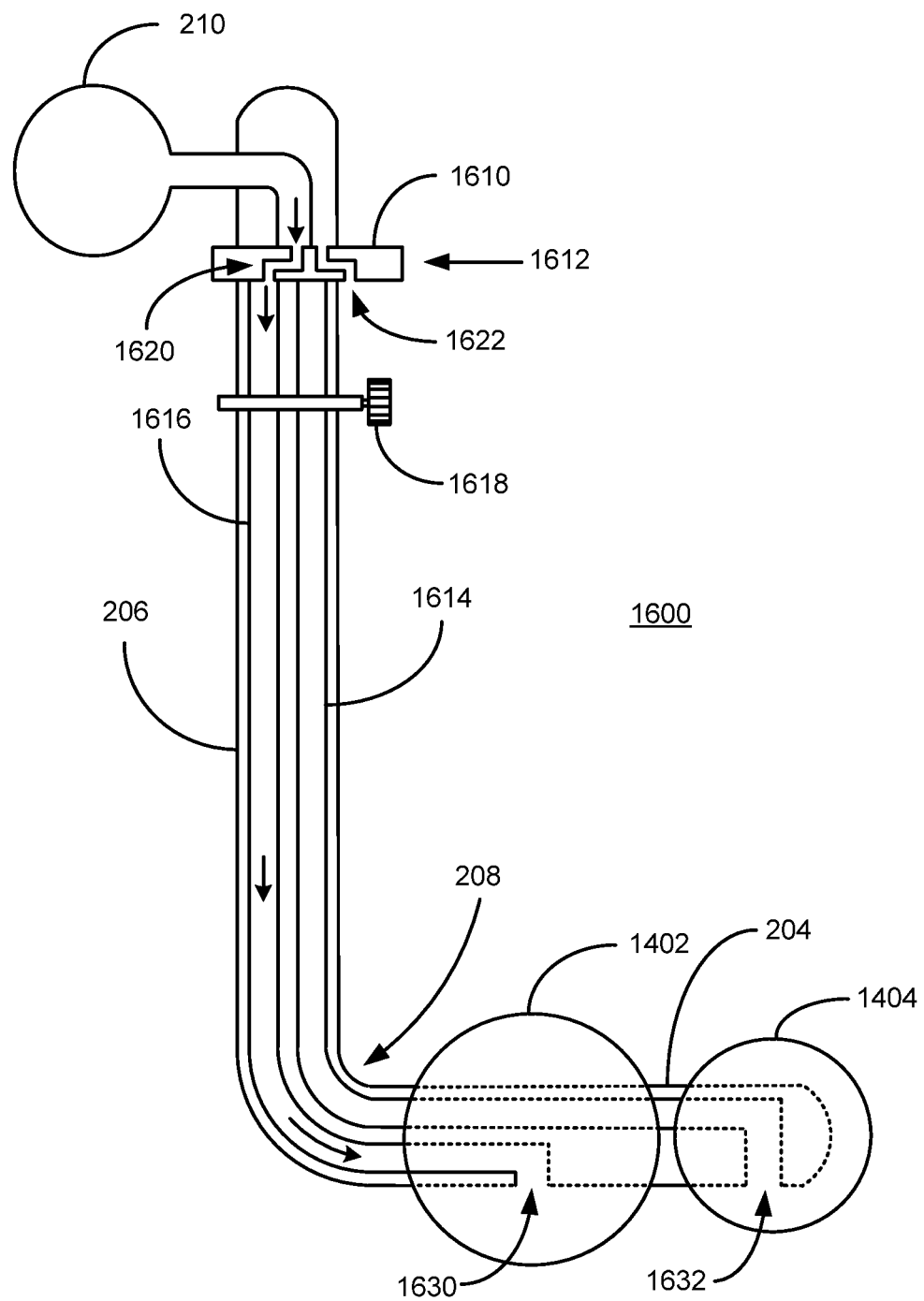
FIG. 16 depicts an embodiment of a recto-cystocele dual balloon expandable sheath device consistent with embodiments of the present invention.

FIG. 16 depicts an embodiment of a recto-cystocele dual balloon expandable sheath device 1600 consistent with embodiments of the present invention. Though a variety of ways to inflate the first balloon portion 1402 and the second balloon portion 1404 are contemplated, one embodiment is depicted here for illustrative purposes. In this embodiment, the recto-cystocele device 1600 possesses a sliding linear valve device 1610 that is adapted to direct flow to either the first passageway 1616 to inflate the first balloon portion 1402 via the first outlet 1630, or to the second passageway 1614 to inflate the second balloon portion 1404 via the second outlet 1632. As depicted, the sliding valve device 1610 is positioned such that the first valve passageway 1620 is open to provide flow from the inflation bulb 210 (or other inflation means) to the first passageway 1616 out the first outlet 1630 to inflate the first balloon portion 1402. The second valve passageway 1622 is in a closed position, thus preventing flow to the second balloon portion 1404 (which is shown inflated). To switch from the first valve passageway 1620 to the second valve passageway 1622, an end user will slide the sliding valve device 1610 in the direction shown by arrow 1612. Likewise, to switch from the second valve passageway 1622 to the first valve passageway 1620, the end user will slide the sliding valve device 1610 in the direction opposite the arrow 1612. Also provided is a release valve 1618 that is opened when the end user wishes to deflate the first balloon portion 1402 and the second balloon portion 1404.

Other embodiments to inflate the first balloon portion 1402 and the second balloon portion 1404 include a single passageway with a first outlet leading to the first balloon portion 1402 and a second outlet leading to the second balloon portion 1404 with backflow valves that that can be released by a release valve or other mechanism. Yet other embodiments contemplate inflating the first balloon portion 1402 and the second balloon portion 1404 with independent inflation sources (dual bulbs 210, for example).

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, additional expansion elements/devices to expand the expandable sheath can be used in a consistent manner with embodiments of the present invention while still maintaining substantially the same functionality without departing from the scope and spirit of the present invention. Another example can include various additional devices (manual, motorize, pneumatic, etc) used to expand or contract the expandable sheath without departing from the scope and spirit of the present invention. Yet, other embodiments can include multiple sheaths to accomplish the end result without departing from the scope and spirit of the present invention. The preferred embodiments described herein are directed to a rectocele device and a cystocele device, which accordingly is not intended for uses beyond the scope and spirit of addressing a rectocele or cystocele of a woman.

It will be clear that the claimed invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the claimed invention disclosed and as defined in the appended claims. Accordingly, it is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

What is claimed is:

1. A recto-cystocele device adapted to be inserted in a vagina of a woman through a vaginal opening, the recto-cystocele device comprising:
    a handle;
    a paddle, wherein the handle and the paddle are distinguished by a bend in the recto-cystocele device which forms essentially an L-shaped unit, the bend possessing a sufficient radius adapted to avoid contact with a pelvic region of the woman and the recto-cystocele device;
    at least one expandable sheath located on the paddle that is adapted to be expanded in the vagina of the woman after being inserted therein, the woman having a posterior side and an anterior side, the expandable sheath further adapted to be-in contact with at least an upper portion of the vagina that includes a posterior fornix of the vagina and a lower portion of the vagina that does not include the posterior fornix, the handle, which is configured not to go into the vagina, is adapted to be held and manually manipulated by the woman to translate directional pressure against the posterior fornix and the lower portion of the vagina via the expandable sheath when expanded, the handle further configured to extend towards the anterior side of the woman when the paddle is disposed in the vagina.

2. The recto-cystocele device of claim 1 wherein the bend extends between 0.5 inches and 5.0 inches from the paddle.

3. The recto-cystocele device of claim 1 wherein the bend possesses a radius of between 0.5 inches and 3.0 inches.

4. The recto-cystocele device of claim 1 further comprising a replaceable sleeve that covers the expandable sheath during each use.

5. The recto-cystocele device of claim 1 further comprising a means for expanding the expandable sheath.

6. The recto-cystocele device of claim 1 wherein the L-shaped unit possesses an angle that is essentially ninety degrees between the handle and the paddle.

7. The recto-cystocele device of claim 1 wherein the expandable sheath extends to at least the distal end of the paddle.

8. The recto-cystocele device of claim 1 wherein said expandable sheath comprises a first balloon portion that is disposed on said paddle between said bend and the distal end of said paddle wherein said first balloon portion is adapted to be in contact with the lower portion of the vagina when inflated and a second balloon portion that is disposed on said paddle and extends beyond the distal end of said paddle is adapted to be in contact with the fornix region of the vagina when inflated.

9. The recto-cystocele device of claim 8 wherein only the second balloon portion is adapted to contacts the posterior fornix when expanded.

10. The recto-cystocele device of claim 8 wherein the first balloon portion extends from beyond the bend to no less than one half of an inch from the distal end of the paddle and the second balloon portion extends at least one half of an inch beyond the distal end of the paddle.

11. The recto-cystocele device of claim 8 wherein the first balloon portion and the second balloon portion are separated by an essentially non-expandable section.

12. A method to assist stool evacuation and urine voiding for a woman, the method comprising:
    providing a device with a handle and a paddle, the handle and the paddle are delineated by a bend in the device, an expandable sheath located on the paddle;
    grasping the handle;
    inserting the paddle through a vaginal opening in a vagina of the woman by the woman before the woman has a bowel movement, or urinating event, or both, the handle extending towards a front side of the woman;
    expanding the expandable sheath inside of the vagina at least until the expandable sheath is in contact with a fornix of the vagina and a portion of the vagina that does not include the fornix;
    manipulating the handle to lift the fornix away from the vaginal opening via the expandable sheath when expanded;
    withdrawing the paddle from the vagina by the woman after the woman has the bowel movement, or the urinating event, or both.

13. The method of claim 12 wherein the handle is adapted to not be in contact with a pelvic region of the woman.

14. The method of claim 12 wherein the expandable sheath comprises a first balloon portion contacting the fornix of the vagina and a second balloon portion contacting the portion of the vagina that does not include the fornix when inserted in the vagina.

15. The method of claim 12 wherein the handle and the paddle forms essentially an L-shaped unit.

16. A recto-cystocele device adapted to be inserted in a vagina of a woman by the woman through a vaginal opening, the recto-cystocele device comprising:
   a handle adapted to be grasped by the woman;
   a paddle, wherein the handle and the paddle are distinguished by a bend in the recto-cystocele device which forms essentially an L-shaped unit, the bend possessing a sufficient radius adapted to avoid contact of the recto-cystocele with a pelvic region of the woman;
   a first expandable balloon located on the paddle between the bend and at least one half of an inch shy of the distal end of the paddle and a second expandable balloon that extends beyond the distal end of the paddle, the paddle is adapted to be inserted by the woman in the woman's vagina and the first and the second balloons expanded therein, the second expandable balloon adapted to be in contact with at least a fornix of the vagina and the first expandable balloon adapted to be in contact with a portion of the vagina that does not include the fornix, the handle, which does not go into the vagina and adapted to extend towards the anterior side of the woman, is adapted to be manually manipulated by the woman to translate directional pressure against the fornix via the second expandable balloon and the portion of the vagina that does not include the fornix via the second expandable balloon when expanded.

17. The method of claim 12 further comprising manipulating the handle to provide directional pressure in all directions of the vagina while remaining in contact with the fornix.

18. The method of claim 17 further comprising directing said directional pressure to support a uterus, a rectrouterine pouch, or a rectum all associated with the woman to mitigate organ prolapse in the woman.

19. The method of claim 12 wherein the expanding step is accomplished with an inflation bulb when manually squeezed.

20. The method of claim 12 wherein the paddle possesses a distal end that is tapered so that the distal end is smaller than where the paddle meets the handle.

* * * * *